United States Patent [19]

Feeney, Jr.

[11] Patent Number: 5,267,977
[45] Date of Patent: Dec. 7, 1993

[54] NO-STICK SYRINGE

[76] Inventor: Richard J. Feeney, Jr., 630 Thomas Loop Rd., Sevierville, Tenn. 37862

[21] Appl. No.: 968,365

[22] Filed: Oct. 29, 1992

[51] Int. Cl.⁵ ............................................. A61M 5/32
[52] U.S. Cl. ..................................... 604/198; 604/263
[58] Field of Search ........................ 604/192, 198, 263

[56] References Cited

U.S. PATENT DOCUMENTS

| | | | |
|---|---|---|---|
| 4,425,120 | 1/1984 | Sampson et al. | 604/263 |
| 4,723,943 | 2/1988 | Spencer | 604/263 |
| 4,790,827 | 12/1988 | Haber et al. | |
| 4,813,426 | 3/1989 | Haber et al. | 604/198 |
| 4,826,490 | 5/1989 | Byrne et al. | |
| 4,850,977 | 7/1989 | Bayless | |
| 4,874,383 | 10/1989 | McNaughton | 604/198 |
| 4,900,311 | 2/1990 | Stern et al. | 604/198 |
| 4,932,940 | 6/1990 | Walker et al. | 604/263 |
| 4,961,730 | 10/1990 | Poncy | 604/198 |
| 4,994,045 | 2/1991 | Ranford | 604/198 |
| 5,002,533 | 3/1991 | Jullien | |
| 5,019,051 | 5/1991 | Hake | 604/198 |
| 5,024,616 | 6/1991 | Ogle, II | 604/198 |
| 5,030,209 | 7/1991 | Wanderer et al. | |
| 5,045,066 | 9/1991 | Scheuble et al. | |
| 5,053,018 | 10/1991 | Talonn | 604/198 |
| 5,088,986 | 2/1992 | Nusbaum | |
| 5,106,379 | 4/1992 | Leap | |
| 5,116,325 | 5/1992 | Paterson et al. | 604/192 |
| 5,116,326 | 8/1992 | Schmidt | |

Primary Examiner—Paul J. Hirsch
Attorney, Agent, or Firm—Richard C. Litman

[57] ABSTRACT

A syringe assembly for reducing the risk of an accidental needle prick. The syringe assembly includes a barrel, a needle lock and hub assembly, and a sheath. The sheath slidably engages the needle lock and hub assembly to selectively conceal or expose the needle. The needle lock and hub assembly is provided with alignment rail buttons which matingly engage alignment rails longitudinally disposed interiorly of the sheath, permitting a limited axial travel of the sheath. A locking chamber and an restrictive passage communicate with the alignment rails which are engagable with a respective adjustment rail button guide to enable the sheath to be locked in a protective posture. The engagement and disengagement of the alignment rail buttons and the locking chambers each produce an audible indication as to whether the sheath is locked to conceal the needle or unlocked to expose the needle. Further, the sheath is transparent so as to provide a visual indication that the alignment rail buttons are engaged with the locking chambers. The transparent sheath also enables the user to observe the orientation of the needle through the sheath.

5 Claims, 1 Drawing Sheet

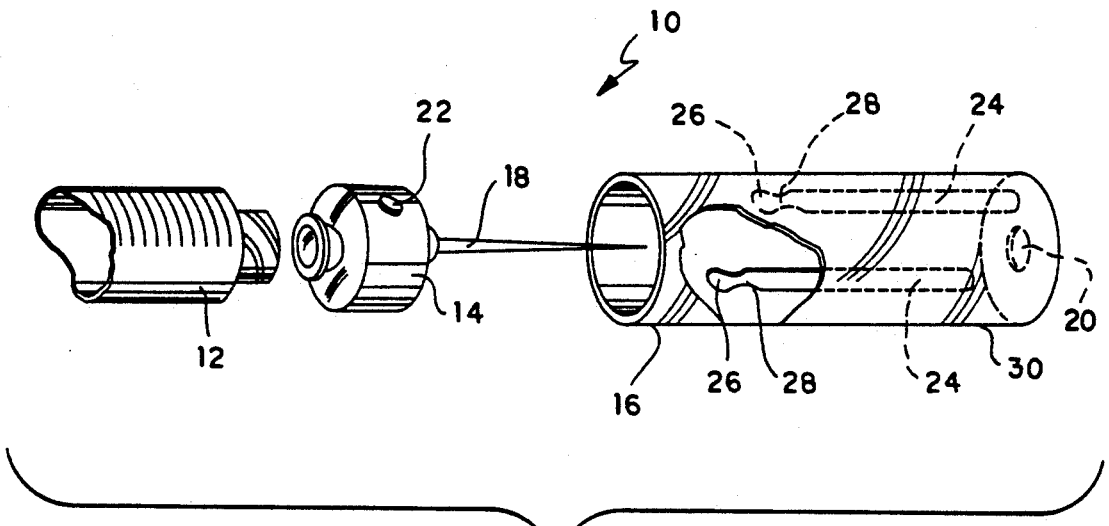
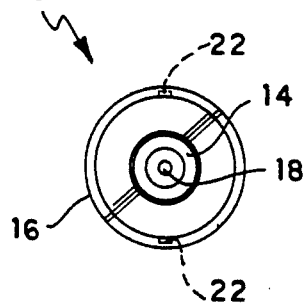
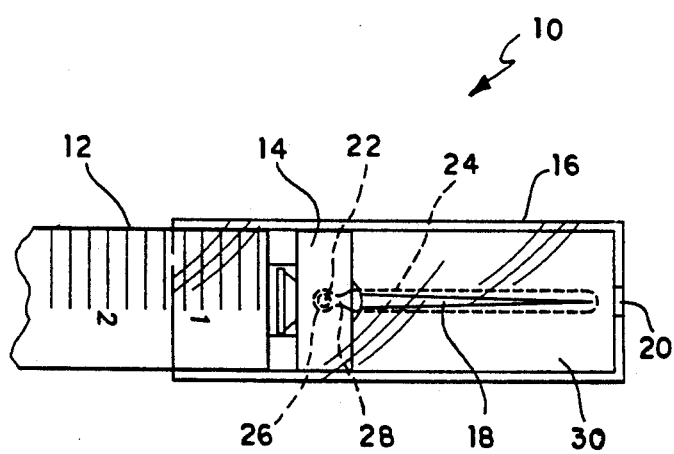
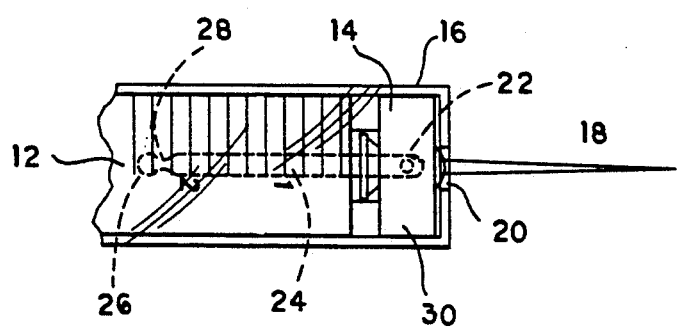
FIG. 1
FIG. 2
FIG. 3
FIG. 4

NO-STICK SYRINGE

BACKGROUND OF THE INVENTION

1. Field of the Invention

The present invention relates to a syringe assembly devised to reduce the risk of an accidental needle prick. The syringe assembly includes a sheath which is slidably engagable with a needle lock and hub assembly so as to permit the sheath to be axially adjustable to selectively lock the sheath in or unlock the sheath from a protective posture, thus concealing and exposing the needle, respectively.

2. Description of the Prior Art

Health care professionals have become increasingly susceptible to the hazards associated with accidental needle strikes during the sheathing of a syringe after an injection has been completed. It has been found that infectious diseases can be transmitted through the handling or disposal of syringes after use. Accidents caused by inadvertent needle pricks may require a blood test for such diseases as AIDS and hepatitis. The corresponding cost and inefficiencies associated with these tests could result in considerable waste, which may be particularly damaging to a health care facility which is striving to cut costs.

Protective sleeves for syringes are well known in the art. One such sleeve is shown in U.S. Pat. No. 4,790,827 issued Dec. 13, 1988 to Terry M. Haber et al. Haber et al. disclose several species of a shielded safety syringe having a protective sleeve engaging a syringe barrel and including a plurality of different locking and guide means which cooperatively guide and lock the sleeve relative to the barrel, none of which are similar to the instant invention described hereinafter.

U.S. Pat. No. 4,826,490 issued May 2, 1989 to Phillip O. Byrne et al. describes safety device for a hypodermic needle having a sheath slidably engagable with a needle housing. The sheath includes a spigot which slides along a channel in the housing and engages a well to lock the sheath in a position concealing the needle.

U.S. Pat. No. 4,850,977 issued Jul. 25, 1989 to William B. Bayless teaches a spring biased sheath held in check by a latch mechanism which when released, will enable the sheath to enclose the needle within the sheath.

U.S. Pat. No. 5,002,533 issued Mar. 26, 1991 to Robert G. Jullien shows a sheath axially extendable from the barrel of a syringe for concealing a needle therein. The sheath must be rotated relative to the barrel in order to lock the sheath in the extended position.

U.S. Pat. No. 5,030,209 issued Jul. 9, 1991 to Alan A. Wanderer et al. describes a protective sheath slidably engaging the needle support. The sheath has a slot with widened openings at either end while the needle support includes a depressible tab having a wider portion which will fit in either of the wider portions of the slot so as to lock the sheath in either a retracted or extended position.

U.S. Pat. No. 5,045,066 issued Sep. 3, 1991 to Gustav A. Scheuble et al. shows a needle with a protective sheath. A hub mountable on the base of the barrel has diametrically opposed tabs engagable with openings in the sheath to lock in the sheath an extended position.

U.S. Pat. No. 5,088,986 issued Feb. 18, 1992 to Michael J. Nusbaum discloses a safety syringe having an actuator operable by rotating a handle to shift a sheath to a retracted position, compressing a spring. A latch locks the sheath and the actuator in the retracted position. By releasing the latch, the actuator and the sheath are returned to the extended position, concealing the needle.

U.S. Pat. No. 5,106,379 issued Apr. 21, 1992 to E. Jack Leap shows a syringe assembly having a sheath that is slidably carried by the barrel of the syringe. A latch is provided to retain the sheath in a retracted position. By pushing up on the latch, the sheath is released to extend and conceal the needle. The sheath includes an L-shaped slot which receives a boss projecting from the barrel. To lock the sheath into an extended position, the sheath must be rotated to move the boss into the small leg of the L.

U.S. Pat. No. 5,116,326 issued May 26, 1992 to David A. Schmidt teaches an hypodermic needle sheath having an extension. The extension has two spaced apart grooves which engage a flange located on the barrel to hold the sheath in an extended or a retracted position.

None of the above inventions and patents, taken either singly or in combination, is seen to disclose or suggest the instant invention as claimed.

SUMMARY OF THE INVENTION

The present invention relates to a syringe assembly for reducing the risk of an accidental needle prick. The syringe assembly includes a barrel, a needle lock and hub assembly, and a sheath. The barrel and the needle lock and hub assembly are joined to one another in a conventional manner. The sheath slidably engages the needle lock and hub assembly to selectively conceal or expose the needle. The needle lock and hub assembly is provided with alignment rail buttons which matingly engage alignment rails longitudinally disposed interiorly of the sheath, permitting a limited axial travel of the sheath. A locking chamber and an associated restrictive passage are located at the proximal end of the alignment rails which enable the sheath to be locked in a protective posture. By axially adjusting the sheath, the alignment rail buttons may be forced through the restrictive passages to engage the locking chambers. When the alignment rail button is passed through the restrictive passage, an audible indication is produced which ensures the user that the sheath is locked in the protective posture. The sheath is transparent to provide a visual indication that the alignment rail buttons are engaged with the locking chambers, further ensuring the user that the sheath is locked in the protective posture. To expose the needle, the sheath is axially adjusted to disengage the alignment rail buttons from the locking chambers. Again, an audible indicator is produced. This alerts the user that the alignment rail buttons have been disengaged from the respective locking chambers. The location of the needle relative to the sheath is observable through the transparent peripheral walls of the sheath. This enables the user to remain clear of the needle as it passes through an opening in the distal end of the sheath. Once the syringe assembly has been used, the sheath may be locked in the protective posture prior to discarding the syringe assembly.

Accordingly, it is a principal object of the invention to provide a syringe assembly which reduces the risk of an inadvertent needle strike and which includes a barrel, a needle lock and hub assembly, and a sheath slidably engaging the needle lock and hub assembly to selectively lock the sheath in a protective posture or unlock the sheath from the protective posture.

It is another object of the invention to provide a syringe assembly having a needle lock and hub assembly provided with alignment rail buttons which matingly engage alignment rails disposed interiorly of the sheath to cooperatively limit the travel of the sheath.

It is a further object of the invention to provide a syringe assembly comprises a sheath having alignment rails in communication with restrictive passages and locking chambers which produce an audible indication of the attitude of the sheath.

Still another object of the invention is to provide a syringe assembly comprising a transparent sheath which provides a visual indication of the attitude of the sheath as well as a visual indication of the location of the needle relative to the sheath, thus enabling the user to remain clear of the needle as it is being exposed.

Yet another object of the invention is to provide a syringe assembly, whereby after the syringe assembly has been used, the sheath may be locked in the protective posture prior to discarding the same.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a perspective of the present invention.

FIG. 2 is an end view of the present invention showing the alignment rail buttons.

FIG. 3 is a top view of the present invention showing the sheath in a protective posture.

FIG. 4 is a top view of the present invention showing the sheath adjusted so as to expose the needle.

Similar reference characters denote corresponding features consistently throughout the attached drawings.

DETAILED DESCRIPTION OF THE PREFERRED EMBODIMENT

The present invention, as shown in FIGS. 1 and 2, is a syringe assembly 10 devised to reduce the risk of an accidental needle prick. The syringe assembly 10 comprises a conventional barrel 12, a needle lock and hub assembly 14, and a sheath 16. The barrel 12 and the needle lock and hub assembly 14 may be fabricated separately then affixed to one another in any conventional manner to provide a sealed syringe assembly 10. The sheath 16 slidably engages the needle lock and hub assembly 14 to selectively conceal the needle or cannula 18 therein as shown in FIG. 3 or expose the needle 18 through a concentrically disposed opening 20 through the distal end of the sheath 16 as shown in FIG. 4. The needle lock and hub assembly 14 has protruding therefrom two opposingly directed, alignment rail buttons 22. The sheath 16 is provided with two longitudinally disposed, elongated alignment rails 24 being spaced apart from one another 180 degrees about the circumference of the sheath 16. Each alignment rail button 22 matingly engages a respective alignment rail 24 permitting a limited axial travel of the sheath 16. A locking chamber 26 and an associated restrictive passage 28 are located at the proximal end of each alignment rail 24 to permit the sheath 16 to be locked in a protective posture.

As shown in FIG. 3, by axially adjusting the sheath 16, the alignment rail buttons 22 may be each simultaneously forced through a respective restrictive passage 28 to engage a respective locking chamber 26. When the alignment rail button 22 is passed through the restrictive passage 28, an audible indication is produced in the form of a snapping or a clicking sound. This alerts the user or the health care professional (not shown) that the alignment rail buttons 22 are locked in position, residing in the locking chambers 26, and that the sheath 16 is, in turn, locked in the protective posture, thus concealing the needle 18 within the sheath 16. The sheath 16 is preferably fabricated of a transparent material so as to also provide a visual indication that the alignment rail buttons 22 have each engaged the locking chambers 26. This further assures the user that the sheath 16 is locked in the protective posture.

To expose the needle 18, the sheath 16 may be axially adjusted to simultaneously disengage the alignment rail buttons 22 from the respective locking chambers 26. Again, a snapping or clicking noise is produced, this time to alert the user that the alignment rail buttons 22 have been disengaged from the respective locking chambers 26. The location of the needle 18 relative to the sheath 16 may be observed through the transparent peripheral walls 30 of the sheath 16. This enables the user to remain clear of the needle 18 as the same passes through the opening 20 in the distal end of the sheath 16. Once the syringe assembly 10 has been used, the sheath 16 may be adjusted to lock the needle 18 in the protective posture prior to discarding the syringe assembly 10.

It is to be understood that the present invention is not limited to the sole embodiment described above, but encompasses any and all embodiments within the scope of the following claims.

I claim:

1. A syringe assembly for reducing risk of accidental needle strikes, said syringe assembly comprising:
   a barrel;
   a needle lock and hub assembly affixed to said barrel;
   a sheath slidably engageable with said needle lock and hub assembly to selectively conceal a needle within said sheath and expose said needle through a concentrically disposed opening through a distal end of said sheath;
   at least one alignment rail button protruding from a solid outer surface of said needle lock and hub assembly;
   at least one longitudinal, elongated alignment rail disposed on an interior surface of the sheath for receiving said at least one alignment rail button, said at least one alignment rail button being restricted to travel within said at least one alignment rail to limit axial and circumferential movement of said sheath relative to said barrel; and
   said at least one alignment rail including a locking chamber and a restrictive passage located at a proximal end of said at least one alignment rail; whereby
   said at least one alignment rail button travels through said restrictive passage to produce an audible indicator when entering said locking chamber to lock said sheath in an extended position to thereby conceal said needle within said sheath, and to produce an audible indicator when exiting said locking chamber to unlock said sheath with said extended position to thereby retract said sheath to expose said needle through said opening in said distal end of said sheath.

2. The syringe assembly according to claim 1, further including a plurality of longitudinal, elongated alignment rails spaced apart and disposed on an interior surface of said sheath.

3. The syringe assembly according to claim 2, further including a plurality of alignment rail buttons, each of said plurality of alignment rail buttons being matingly engagable with a respective one of said plurality of alignment rails.

4. The syringe assembly according to claim 3, wherein each of said plurality of alignment rails includes a locking chamber and restrictive passage located at a proximal end of each of said plurality alignment rails, whereby when said sheath is axially adjusted, each one of said plurality of alignment rail buttons is simultaneously forced through a respective one of said restrictive passages to engage a respective one of said locking chambers.

5. The syringe assembly according to claim 1, wherein said sheath is fabricated of a transparent material so as to provide a visual location of said needle relative to said sheath and a visual indication that said alignment rail button has engaged said locking chamber, thus far ensuring that said sheath is locked in said extended position.

* * * * *